United States Patent
Wise et al.

(10) Patent No.: US 9,138,429 B2
(45) Date of Patent: Sep. 22, 2015

(54) PROCESS OF FORMING CRYSTALS FOR USE IN A PERSONAL CARE COMPOSITION

(75) Inventors: Geoffrey Marc Wise, Reading, OH (US); Nicholas William Geary, Mariemont, OH (US); David Edward Rose, Hayes End (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/528,980

(22) Filed: Jun. 21, 2012

(65) Prior Publication Data

US 2012/0329768 A1  Dec. 27, 2012

Related U.S. Application Data

(60) Provisional application No. 61/500,338, filed on Jun. 23, 2011.

(51) Int. Cl.
| | |
|---|---|
| *A61K 31/555* | (2006.01) |
| *A61K 31/4365* | (2006.01) |
| *A61K 8/37* | (2006.01) |
| *A61K 8/46* | (2006.01) |
| *A61Q 19/10* | (2006.01) |
| *A61Q 5/02* | (2006.01) |
| *A61Q 17/00* | (2006.01) |
| *A61K 8/06* | (2006.01) |

(52) U.S. Cl.
CPC .............. *A61K 31/4365* (2013.01); *A61K 8/062* (2013.01); *A61K 8/375* (2013.01); *A61K 8/463* (2013.01); *A61Q 5/02* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 4,717,501 A | 1/1988 | Hirota et al. |
| 4,741,855 A | 5/1988 | Grote et al. |
| 4,830,774 A | 5/1989 | LaPetina et al. |
| 4,885,107 A | 12/1989 | Wetzel |
| 5,085,857 A | 2/1992 | Reid et al. |
| 5,154,847 A | 10/1992 | LaPetina et al. |
| RE34,584 E | 4/1994 | Grote et al. |
| 5,403,508 A | 4/1995 | Reng et al. |
| 5,529,721 A | 6/1996 | Salka et al. |
| 5,560,873 A | 10/1996 | Chen et al. |
| 5,646,106 A | 7/1997 | Chen et al. |
| 5,674,511 A | 10/1997 | Kacher et al. |
| 5,711,899 A | 1/1998 | Kawa et al. |
| 5,763,505 A | 6/1998 | Derian et al. |
| 5,888,487 A | 3/1999 | Baumoeller et al. |
| 5,925,340 A | 7/1999 | Valdes et al. |
| 5,925,604 A | 7/1999 | Chen et al. |
| 6,037,407 A | 3/2000 | Derian et al. |
| 6,121,331 A | 9/2000 | Ansmann et al. |
| 6,147,124 A | 11/2000 | Ansmann et al. |
| 6,165,955 A | 12/2000 | Chen et al. |
| 6,228,831 B1 | 5/2001 | Ansmann et al. |
| 6,235,702 B1 | 5/2001 | Ansmann et al. |
| 6,306,916 B1 | 10/2001 | Ansmann et al. |
| 6,391,834 B1 | 5/2002 | Schelges et al. |
| 6,417,146 B1 | 7/2002 | Miyajima et al. |
| 6,417,294 B1 | 7/2002 | Obuchi et al. |
| 6,656,975 B1 | 12/2003 | Christiano et al. |
| 6,727,217 B1 | 4/2004 | Nieendick et al. |
| 6,835,700 B1 | 12/2004 | Nieendick et al. |
| 7,056,379 B2 | 6/2006 | Nieendick et al. |
| 7,176,171 B2 | 2/2007 | Nieendick et al. |
| 7,183,340 B2 | 2/2007 | Harashina et al. |
| 7,256,224 B2 | 8/2007 | Martin et al. |
| 7,268,107 B2 | 9/2007 | Nieendick et al. |
| 7,309,685 B2 | 12/2007 | Wachter et al. |
| 7,354,891 B2 | 4/2008 | Arai |
| 7,381,417 B2 | 6/2008 | Gamez-Garcia |
| 7,578,995 B2 | 8/2009 | Frantz et al. |
| 7,589,051 B2 | 9/2009 | Erazo-Majewicz et al. |
| 7,910,535 B2 | 3/2011 | Panandiker et al. |
| 8,003,589 B2 | 8/2011 | Panandiker et al. |
| 8,030,266 B2 | 10/2011 | Hosoya et al. |
| 8,119,168 B2 | 2/2012 | Johnson et al. |
| 8,188,026 B2 | 5/2012 | Panandiker et al. |
| 8,236,745 B2 | 8/2012 | Panandiker et al. |
| 2003/0044441 A1 | 3/2003 | Schmid et al. |
| 2003/0143181 A1 | 7/2003 | Hensen et al. |

(Continued)

FOREIGN PATENT DOCUMENTS

| | | |
|---|---|---|
| EP | 568848 | 11/1993 |
| EP | 581193 | 2/1994 |

(Continued)

OTHER PUBLICATIONS

Bolzinger et al (Colloids and Surfaces A:Physiochem Eng Aspects 299:93-100, 2007).*

(Continued)

*Primary Examiner* — Craig Ricci
(74) *Attorney, Agent, or Firm* — Angela K. Haughey

(57) ABSTRACT

A method of making a stable detersive surfactant containing personal care composition comprising the steps of emulsifying a stabilizing agent in the presence of anionic surfactant to form an emulsion containing droplets having a particle size of from about 0.1 to about 10 um. These particles are then cooled to form a stabilizing premix at a rate of about 10 to about 1000 C/min to form crystals from the droplets, the crystals having a maximum dimension of about 0.1 to about 3 um. These crystals are then added to a detersive surfactant containing personal care composition to increase stability.

15 Claims, 1 Drawing Sheet

(56) References Cited

U.S. PATENT DOCUMENTS

| | | |
|---|---|---|
| 2004/0086470 A1 | 5/2004 | Nieendick et al. |
| 2004/0105831 A1* | 6/2004 | Frantz et al. ............... 424/70.12 |
| 2004/0120974 A1 | 6/2004 | Gesslein |
| 2004/0247630 A1 | 12/2004 | Seipel et al. |
| 2005/0000390 A1 | 1/2005 | Nieendick et al. |
| 2005/0079193 A1 | 4/2005 | Nieendick et al. |
| 2005/0158270 A1 | 7/2005 | Frantz et al. |
| 2005/0181041 A1 | 8/2005 | Goldman |
| 2006/0127427 A1 | 6/2006 | Vernice et al. |
| 2008/0063618 A1 | 3/2008 | Johnson et al. |
| 2008/0138442 A1 | 6/2008 | Johnson et al. |
| 2008/0311060 A1 | 12/2008 | Sakuta et al. |
| 2009/0214608 A1 | 8/2009 | Monin et al. |
| 2011/0034366 A1 | 2/2011 | Panandiker et al. |
| 2011/0163263 A1 | 7/2011 | Hosoya et al. |

FOREIGN PATENT DOCUMENTS

| | | |
|---|---|---|
| EP | 0520551 B1 | 3/1996 |
| EP | 930356 | 8/1999 |
| EP | 684302 | 11/1999 |
| EP | 1060737 | 12/2000 |
| EP | 1060740 | 12/2000 |
| EP | 1061121 | 12/2000 |
| EP | 1061122 | 12/2000 |
| EP | 1065258 | 1/2001 |
| EP | 1067175 | 1/2001 |
| EP | 1200062 | 5/2002 |
| EP | 930872 | 6/2002 |
| EP | 1343456 | 9/2003 |
| EP | 999822 | 9/2004 |
| EP | 1002038 | 9/2004 |
| JP | 8231985 | 9/1996 |
| JP | 2003-155214 | 5/2003 |
| JP | 2010-053037 | 3/2010 |
| WO | 92/13512 | 8/1992 |
| WO | 97/13498 A1 | 4/1997 |
| WO | 01/25378 A2 | 4/2001 |
| WO | 03/066796 A1 | 8/2003 |
| WO | 2004/028676 A1 | 4/2004 |
| WO | 2008-040770 | 4/2008 |

OTHER PUBLICATIONS

PCT International Search Report and Written Opinion for PCT/US2012/043559 dated Oct. 7, 2014.

* cited by examiner

PROCESS OF FORMING CRYSTALS FOR USE IN A PERSONAL CARE COMPOSITION

CROSS REFERENCE TO RELATED APPLICATION

This application claims the benefit of U.S. Provisional Application Ser. No. 61/500,338 filed Jun. 23, 2011.

FIELD OF THE INVENTION

The invention relates to the process of forming crystals for addition to a personal care composition to increase the stability of the personal care composition.

BACKGROUND OF THE INVENTION

Personal care compositions often contain materials which provide both pearlescence and stability to the composition. A stable personal care composition is important to consumers since a loss of stability leads to a separated product. Besides being aesthetically unattractive to consumers, a separated personal care composition can lead to products in which either the top or bottom layer of the composition is deficient in critical actives.

Stabilizing agents are typically crystallized out of a hot solution or an emulsion and then added to personal care products in order to improve product stability. Typically, the process of forming a concentrated premix of crystals of the desired crystal morphology is a two step process in which the stabilizing agent first diffuses from droplets in an emulsion into a solution where crystallization then occurs. This method is slow, costly, and can require ingredients that provide minimal or no functional value in the final personal care composition.

Accordingly, there is a need for a more efficient manufacturing process to crystallize stabilizing agents more efficiently for use in personal care compositions. In addition, there is a need for crystals with a morphology which imparts a greater stability to personal care compositions. Furthermore, there is a need for crystals which can be easily blended into the personal care composition in a timely and cost effective manner.

SUMMARY OF THE INVENTION

According to one embodiment, a method of making a stable, detersive surfactant-containing anti-microbial personal care composition comprising: (a) emulsifying from 4% to 30% of a stabilizing agent in the presence of from 2% to 30% of an anionic surfactant to form an emulsion at a temperature of from 1° C. to 50° C. above the melting point of the stabilizing agent, wherein the emulsion contains droplets having a particle size of from 0.1 micron to 10 micron; then (b) cooling the emulsion to form a stabilizing premix at a rate of from 10° C./min to 1000° C./min to a temperature of from 5° C. to 50° C. below the melting point of the stabilizing agent to form crystals from the droplets, the crystals having a maximum dimension of from 0.1 micron to 3 micron and an aspect ratio of from 2 to 1000; and then (c) adding the stabilizing premix to a detersive surfactant-containing anti-microbial personal care composition.

The method according to the previous embodiment, wherein the stabilizing agent is ethylene glycol distearate. The method according to any preceding embodiments, wherein the stabilizing premix comprises from 4% to 40% of the total detersive surfactant-containing anti-microbial personal care composition. The method according to any preceding embodiments, wherein the anionic surfactant is selected from the group consisting of alkyl sulfate, alkyl ether sulfate, or combinations thereof. The method according to the previous embodiment, wherein the alkyl ether sulfate has a molar ethoxylation ratio of from 0.5 to 5. The method according to any preceding embodiments, wherein the emulsion of the crystallizing agent employs an agitated tank, a static mixer, an orifice plate, a rotor/stator mill, high energy homogenizer, or combinations thereof, preferably wherein the high energy homogenizer is a sonolator.

The method according to any preceding embodiments, wherein the emulsion is created using a power density of from 1 W/kg to 1000 W/kg. The method according to any preceding embodiments, wherein the stabilizing premix is added to the detersive surfactant-containing anti-microbial personal care composition less than 24 hours after crystallization. The method according to any preceding embodiments, wherein the viscosity of the stabilizing premix is from 50 cP to 20,000 cP. The method according to any preceding embodiments, wherein the cooling of the emulsion employs a heat exchanger in a single pass or recirculation process, preferably wherein the heat exchanger is a scraped wall, plate and frame, or shell and tube heat exchanger.

The method according to any preceding embodiments, wherein the detersive surfactant-containing anti-microbial personal care composition contains an additional structuring agent selected from the group consisting of hydrogenated castor oil, polysaccharides, and combinations thereof. The method according to any preceding embodiments, wherein the detersive surfactant-containing anti-microbial personal care composition contains detersive surfactants selected from the group consisting of anionic surfactants, zwitterionic surfactants, amphoteric surfactants, or combinations thereof. The method according to any preceding embodiments, wherein both the stabilizing premix and the detersive surfactant-containing anti-microbial personal care composition comprise at least 2% of the same anionic surfactant. The method according to any preceding embodiments, wherein the detersive surfactant-containing anti-microbial personal care composition comprises an anti-dandruff active and wherein the anti-dandruff active is ZPT. The method according to any preceding embodiments, wherein the detersive surfactant-containing anti-microbial personal care composition separates less than 4 mm in 30 days when 85 g of the detersive surfactant-containing anti-microbial personal care composition is placed in a 4 cm diameter jar at 40° C.

According to another embodiment, a method of making a stable, detersive surfactant-containing personal care composition comprising: (a) emulsifying from 4% to 30% of a stabilizing agent in the presence of from 2% to 30% of an anionic surfactant and from 0.3% to 10% of an organic fatty acid or alcohol to form an emulsion at a temperature of 1° C. to 50° C. above the melting point of the stabilizing agent, wherein the emulsion contains droplets having a particle size of 0.1 to 10 um; (b) cooling the emulsion to form a stabilizing premix at a rate of 10° C./min to 1000° C./min to a temperature of 5° C. to 50° C. below the melting point of the stabilizing agent to form crystals from the droplets having a maximum dimension of 0.1 micron to 3 micron; and (c) adding the stabilizing premix to a detersive surfactant-containing personal care composition.

The method according to the previous embodiment, wherein the organic fatty acid or alcohol has a carbon chain length of from 8 to 20. The method according to the previous two embodiments, wherein the crystals have an aspect ratio of from 2 to 1000.

DETAILED DESCRIPTION OF THE INVENTION

Figure 1A:
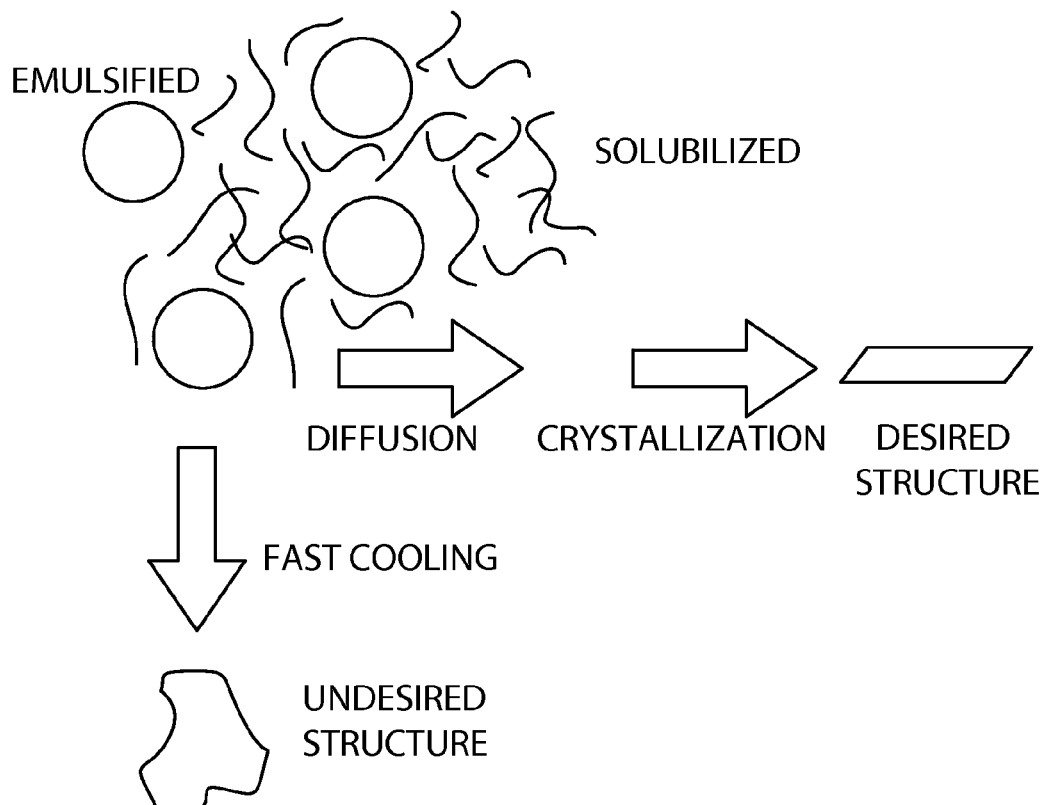
FIG. 1A illustrates the formation of crystals via a solubilized state.

In all embodiments of the invention, all percentages are by weight of the total composition, unless specifically stated otherwise. All ratios are weight ratios, unless specifically stated otherwise.

All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Definitions

As used herein, the term "fluid" includes liquids and gels.

As used herein, the term "emulsion" refers to a dispersion of droplets of fluid inside of another fluid.

As used herein, the term "stabilizing premix" refers to the concentrated dispersion containing the crystallized stabilizing agent to be added to the personal care composition.

As used herein, the term "personal care composition" refers to the combination of detersive surfactant and carrier.

As used herein, the term "personal cleansing composition" includes, unless otherwise indicated, any personal cleansing composition that can be applied to the keratinaceous surfaces of the body including the skin and/or hair. The personal cleansing compositions can be, for example, formulated as cleaning bars, liquids, emulsions, shower gels, powders, sticks, pastes, mouthwashes, foam baths, shave prep products, and devices used for shaving.

As used herein, the articles including "a" and "an" when used in a claim, are understood to mean one or more of what is claimed or described.

As used herein, the terms "include," "includes," and "including," are meant to be non-limiting.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

It has been unexpectedly found that under certain circumstances, crystals can be formed quickly and directly from small emulsified droplets into a crystal morphology that leads to efficient stabilization of personal care compositions. This unexpected process enables proper crystal morphology to occur even when the solubility of the stabilizing agent in the emulsion is small. The new process also significantly reduces the time required in the cooling step, thereby reducing the cost of manufacture.

One common approach for creating crystals from a stabilizing agent involves preparing a mixture containing a relatively dilute amount of crystallizing agent at a temperature above its melting point with a sufficient level of surfactant such that the majority of the crystallizing agent is solubilized prior to crystallization. The crystallization then proceeds directly from the solubilized agent. This method has the advantage of being conducive to quick cooling, but suffers from the fact that the concentration of the crystallizing agent is limited by its solubility in the mixture. Therefore, a large fraction of the total personal care composition must be included in the crystallization step.

A second approach for creating crystals involves making a more concentrated hot mixture, such that the majority of the crystallizing agent is emulsified rather than solubilized. This approach works to reduce the fraction of the personal-care composition included in the crystallization step which in turn reduces the energy required to prepare the crystals. However, until now, this has required a slow rate of cooling. This slower cooling rate occurs because the crystals are formed from the solubilized material, and it takes time for the material to diffuse from the emulsified state into the solubilized state, as illustrated in FIG. 1A. Direct crystallization of the stabilizing agent from the emulsion droplets ordinarily would result in crystals that are too large or the wrong shape to be effective in stabilizing the final personal care composition.

Figure 1B:
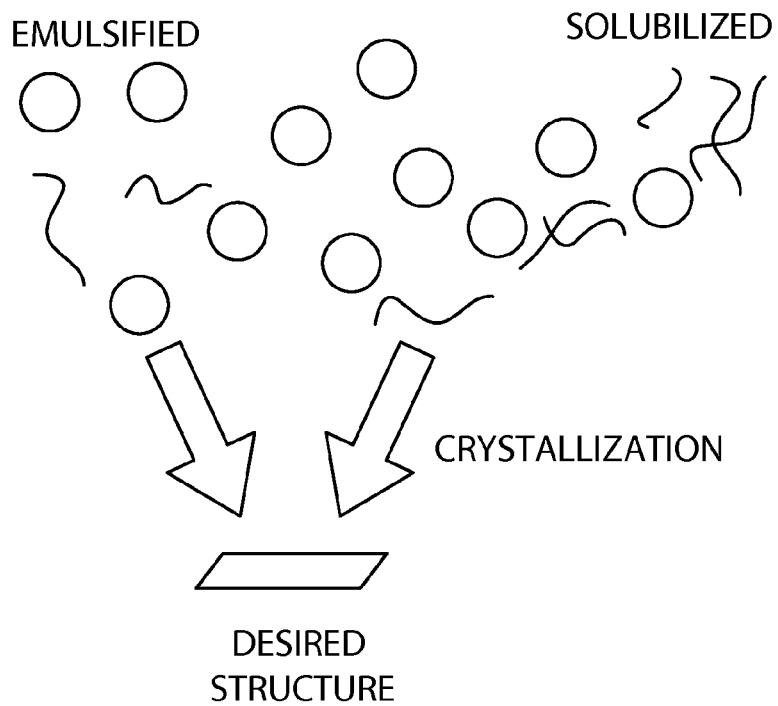
FIG. 1B illustrates the formation of crystals directly from an emulsified state.

It has been surprisingly found that by keeping the particle size of the emulsion in the range of from about 0.1 to about 10 um (um is equivalent to microns), crystals can be formed directly from these particles without having to first diffuse into the liquid matrix, as illustrated in FIG. 1B. In combination with a faster cooling step at a rate of about 10 to about 1000 C/min, crystals are formed with a more anisotropic (needle or plate like) morphology which leads to greater stability when added to a personal care composition. This increased stability is especially important in anti-microbial personal care compositions in which a loss of stability may lead to layers in the products which are deficient in anti-microbial actives. Moreover, the desired crystallization can be effected in the presence of an anionic surfactant that is functionally active in the final personal care composition, eliminating the need for crystal control agents that are of no benefit in the final personal care composition.

In addition, it has unexpectedly been found that the addition of an organic fatty acid or alcohol in the emulsion prior to crystallization dramatically improves personal care composition stability.

Method of Manufacture

A stable detersive surfactant containing anti-microbial personal care composition can be made by the method of: emulsifying from about 4% to about 30% of a stabilizing agent in the presence of from about 2% to about 30% of an anionic surfactant, at a temperature of about 1° C. to about 50° C. above the melting point of the stabilizing agent, to form an emulsion, wherein the emulsion contains droplets having a particle size of about 0.1 to about 10 um; cooling the emulsion to form a stabilizing premix at a rate of about 10 to about 1000 C/min to a temperature of about 5° C. to about 50° C. below the melting point of the stabilizing agent to form crystals from the droplets, the crystals having a mean length as defined by a maximum dimension of about 0.1 to about 3um and an aspect ratio of about 2 to about 1000; and adding the stabilizing premix to a detersive surfactant containing anti-microbial personal care composition.

A stable detersive surfactant containing personal care composition can also be made by the method of: emulsifying from about 4% to about 30% of a stabilizing agent in the presence of from about 2% to about 30% of an anionic surfactant and from about 0.3% to about 10% of an organic fatty acid or alcohol, at a temperature of about 1° C. to about 50° C. above the melting point of the stabilizing agent, to form an emulsion, wherein the emulsion contains droplets having a particle size of about 0.1 to about 10 um; cooling the emulsion to form a stabilizing premix at a rate of about 10 to about 1000 C/min to a temperature of about 5° C. to about 50° C. below the melting point of the stabilizing agent to form crystals from the droplets having a maximum dimension of about 0.1 to about 3um; and adding the stabilizing premix to a detersive surfactant containing personal care composition.

A. Preparation of Emulsion

An emulsion is produced by dispersing a stabilizing agent in the presence of an anionic surfactant at a temperature of about 1° C. to about 50° C. above the melting point of the stabilizing agent. In one embodiment, an emulsion is formed by heating from about 4% to about 30% of a stabilizing agent in the presence of from about 2% to about 30% of an anionic surfactant, at a temperature of about 1° C. to about 50° C. above the melting point of the stabilizing agent, to form an emulsion. In another embodiment, the emulsion is formed at a temperature from about 5° C. to about 20° C. above the melting point of the stabilizing agent.

A high shear mill device may be used to produce the desired particle size of the emulsion. The desired particle size of the emulsion may be formed using an agitated tank, a static mixer, an orifice plate, a rotor/stator mill, high energy homogenizer, or combinations thereof. In one embodiment, the high energy homogenizer is a sonolator. In one embodiment, the emulsion is created using a peak power density of from about 1 to about 1000 W/kg. In another embodiment, from about 1 to about 1000 J/kg of emulsification energy is imparted in a single-pass or recirculation operation.

After emulsification, the emulsion contains droplets having a volume-average particle size of from about 0.1 to about 10 um, or from about 0.2 to about 2 um, as measured by a Horiba LA-950 particle sizer at 70° C. By keeping the particle size within this range, it is possible to form crystals in the later cooling step directly from these droplets without the stabilizing agent having to first move into the continuous phase of the emulsion. The viscosity of the emulsion is from about 1 to about 2000 cP.

B. Formation of Stabilizing Premix

The emulsion is cooled down to form a stabilizing premix at a cooling rate of about 10 to about 1000° C./min to a temperature of about 5° C. to about 50° C. below the melting point of the stabilizing agent. Cooling of the emulsion can occur using a single pass process, a recirculation process, or combinations thereof. In one embodiment, the recirculation process uses a heat exchanger. This heat exchanger can be selected from the group consisting of a scraped wall exchanger, a plate and frame exchanger, or a shell and tube heat exchanger.

The rapid cooling step produces crystals directly from the emulsion droplets. By controlling the emulsion particle size, crystals are formed having a more anisotropic morphology which enhances the stability of the resulting personal care composition. In one embodiment, the crystals have the shape of thin plates as opposed to spherical particles. As used herein, spherical particles have an aspect ratio of less than 3, for which the aspect ratio is defined as the ratio of the maximum to the minimum dimension. Particle size is measured across the largest diameter of the object. Plate-like particles are such that two dimensions of the particle (length and width) are at least 5 times the third dimension (depth or thickness). In another embodiment, the crystals have the shape of needles in which the particle length is at least 5 times the particle width and thickness.

It has been found that small, anisotropic crystals improve the stability of personal care compositions compared to crystals having larger, more spherical structures when added to the composition in the same amount. In one embodiment, an anti-microbial personal care composition containing crystals separates less than 4 mm in about 30 days when 85 g of the anti-microbial personal care composition is placed in a 5 cm jar at 40° C.

The high aspect ratio of the crystals allows them to more efficiently form a stabilizing network in the personal care composition at a given level of the stabilizing agent. The crystals typically have an aspect ratio of from about 2 to about 1000. These crystals have a maximum dimension of from about 0.1 to about 3um. The viscosity of the stabilizing premix after a 24-hour storage period at 25° C. is from about 50 to about 20,000 cP, when measured at 25° C. and a shear rate of 2/sec. The stabilizing premix comprises from about 4% to about 40% of the total personal care composition.

C. Addition of Crystals to Personal Care Composition

The resulting crystal dispersion can subsequently be incorporated into the liquid composition with stirring and without any externally applied heat, either immediately after crystallization or after a storage period of the cooled stabilizing premix. In one embodiment, the stabilizing premix is added to the detersive surfactant containing personal care composition less than twenty four hours after crystallization. The resulting personal care composition has an attractive pearlescent appearance and is stable for months under typical storage conditions. In other words, the resulting product maintains its pearlescent appearance and does not exhibit separation or stratification from the composition matrix.

The detersive surfactant containing composition contains detersive surfactant and a carrier. The detersive surfactant is selected from the group consisting of anionic surfactants, zwitterionic surfactants, amphoteric surfactants, and combinations thereof. In one embodiment, the anionic surfactant in the emulsion is the same as the anionic surfactant in the personal care composition. This prevents the addition of extra materials that have little or no functional value in the final personal care composition.

In one embodiment, the detersive surfactant containing personal care composition contains anti-microbial actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulfide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Examples of anti-microbials include itraconazole, ketoconazole, selenium sulfide and coal tar.

Anti-microbial actives also include anti-dandruff actives. Suitable, non-limiting examples of anti-dandruff actives include: pyridinethione salts, azoles, selenium sulfide, particulate sulfur, and mixtures thereof. Other embodiments include pyridinethione salts, specifically the zinc salt of 1-hydroxy-2-pyridinethione (known as "zinc pyridinethione" or "ZPT"). Such anti-dandruff particulate should be physically and chemically compatible with the essential components of the composition, and should not otherwise unduly impair product stability, aesthetics or performance.

Composition of the Stabilizing Premix

A. Stabilizing Agent

The stabilizing premix comprises from about 4% to about 30% by weight of the personal care composition of a 100% active stabilizing agent. In another embodiment, the stabilizing premix comprises from about 15% to about 25% of stabilizing agent.

Suitable stabilizing agents include monoester and/or diester of alkylene glycols having the formula:

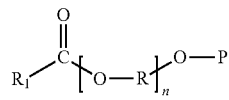

wherein $R_1$ is linear or branched C12-C22 alkyl group;
R is linear or branched C2-C4 alkylene group;
P is selected from H, C1-C4 alkyl or —$COR_2$, $R_2$ is C4-C22 alkyl, in another embodiment C12-C22 alkyl; and
n=1-3.

In one embodiment, the long chain fatty ester has the general structure described above, wherein $R_1$ is linear or branched C16-C22 alkyl group, R is —$CH_2$—$CH_2$—, and P is selected from H, or —$COR_2$, wherein $R_2$ is C4-C22 alkyl, in another embodiment C12- C22 alkyl.

Typical examples are monoesters and/or diesters of ethylene glycol, propylene glycol, diethylene glycol, dipropylene glycol, triethylene glycol or tetraethylene glycol with fatty acids containing from about 6 to about 22, from about 12 to about 18 carbon atoms, such as caproic acid, caprylic acid, 2-ethyhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid, erucic acid, and mixtures thereof.

In one embodiment, ethylene glycol monostearate (EGMS) and/or ethylene glycol distearate (EGDS) and/or polyethylene glycol monostearate (PGMS) and/or polyethyleneglycol distearate (PGDS) are the stabilizing agents used in the composition. There are several commercial sources for these materials. For Example, PEG6000MS® is available from Stepan, Empilan EGDS/A® is available from Albright & Wilson.

B. Anionic Surfactant

The stabilizing premix comprises from about 2% to about 30% of an anionic surfactant, in another embodiment from about 5% to about 25% of an anionic surfactant. In one embodiment, both the stabilizing premix and the personal care composition comprise at least 2% of the same anionic surfactant.

Useful anionic surfactants can themselves be of several different types. For example, water-soluble salts of the higher fatty acids are useful anionic surfactants in the compositions herein. This includes alkali metal soaps such as the sodium, potassium, ammonium, and alkyl ammonium salts of higher fatty acids containing from about 8 to about 24 carbon atoms, and from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Additional non-soap anionic surfactants which are suitable for use herein include the water-soluble salts, the alkali metal, and ammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are a) the sodium, potassium and ammonium alkyl sulfates, especially those obtained by sulfating the higher alcohols ($C_8$-$C_{18}$ carbon atoms) such as those produced by reducing the glycerides of tallow or coconut oil; b) the sodium, potassium and ammonium alkyl polyethoxylate sulfates, particularly those in which the alkyl group contains from 10 to 22, in another embodiment from 12 to 18 carbon atoms, and wherein the polyethoxylate chain contains from 0.5 to 15, in another embodiment from 0.8 to 5 ethoxylate moieties; and c) the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$-$C_{13}$ LAS. In another embodiment, the anionic surfactant is an alkyl ether sulfate having a molar ethoxylation ratio of from about 0.5 to about 5.

C. Co-Crystallizing Agents:

Optionally, co-crystallizing agents such as organic fatty acids and alcohols are used to control the emulsification of the molten stabilizing agent, tune the crystal morphology upon crystallization, and improve the rheology of the stabilizing premix after cooling. These organic fatty acids and alcohols have been unexpectedly found to increase the stability of the resulting crystals in the detersive surfactant containing personal care composition.

The amount of co-crystallizing agent included in the emulsion is the amount sufficient to produce the desired crystal size and size distribution of the stabilizing agents, under a given set processing parameters.

Suitable co-crystallizing agents include but are not limited to fatty acids and/or fatty alcohols having a linear or branched, optionally hydroxyl substituted, alkyl group containing from about 12 to about 22, in another embodiment from about 8 to about 20, in another embodiment from about 16 to about 22, and in another embodiment from about 18 to 20 carbon atoms, such as palmitic acid, linoleic acid, stearic acid, oleic acid, ricinoleic acid, behenyl acid, cetearyl alcohol, hydroxystearyl alcohol, behenyl alcohol, linolyl alcohol, linolenyl alcohol, and mixtures thereof.

In one embodiment where the co-crystallizing agent is present, the stabilizing premix comprises 1-5 wt % C12-C20 fatty acid, C12-C20 fatty alcohol, or mixtures thereof. In another embodiment, the weight ratio between the stabilizing agent and the co-crystallizing agent ranges from about 3:1 to about 10:1, or from about 5:1 to about 20:1.

In one embodiment, the composition comprises 20-65 wt % water; 5-30 wt % sodium alkyl sulfate or alkyl ether sulfate dispersing surfactant; 5-30 wt % long chain fatty ester and 1-5 wt % C12-C22 fatty alcohol or fatty acid, wherein the weight ratio of long chain fatty ester to fatty alcohol and/or fatty acid ranges from about 5:1 to about 20:1, or from about 3:1 to about 10:1.

Detersive Surfactant Containing Personal Care Composition

The composition of the invention may comprise any combination of the following components:

A. Detersive Surfactant

The personal care composition includes a detersive surfactant. The detersive surfactant provides cleaning performance to the composition. The detersive surfactant in turn comprises anionic detersive surfactant, zwitterionic or amphoteric detersive surfactant, or combinations thereof. Various examples and descriptions of detersive surfactants are set forth in U.S. Pat. No. 6,649,155; U.S. patent application Ser. No. 12/103,902; and U.S. Patent Publication 2008/0206355.

The concentration of the anionic surfactant component in the personal care composition should be sufficient to provide the desired cleaning and lather performance, and generally ranges from about 2% to about 50%, from about 8% to about 30%, from about 10% to about 25%, or from about 12% to about 22%.

Anionic surfactants suitable for use in the compositions are the alkyl and alkyl ether sulfates. Other suitable anionic detersive surfactants are the water-soluble salts of organic, sulfuric acid reaction products. Still other suitable anionic detersive surfactants are the reaction products of fatty acids esterified with isethionic acid and neutralized with sodium hydroxide. Other similar anionic surfactants are described in U.S. Pat. Nos. 2,486,921; 2,486,922; and 2,396,278.

Anionic detersive surfactants for use in the personal care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic detersive surfactants for use in the composition herein include those which are known for use in hair care or other personal care cleansing. Concentrations of such amphoteric detersive surfactants range from about 0.5% to about 20%, and from about 1% to about 10%. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric detersive surfactants suitable for use in the personal care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Amphoteric detersive surfactants include cocoamphoacetate, cocoamphodiacetate, lauroamphoacetate, lauroamphodiacetate, and mixtures thereof.

Zwitterionic detersive surfactants include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

B. Aqueous Carrier

The formulations can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Other Optional Components

The personal care composition may further comprise other optional ingredients that are known for use or otherwise useful in compositions. Such optional ingredients are most typically those described in reference books such as the CTFA Cosmetic Ingredient Handbook, Second Edition, The Cosmetic, Toiletries, and Fragrance Association, Inc. 1988, 1992.

Further non-limiting examples of such optional ingredients include perfumes or fragrances, coloring agents or dyes, hair bleaching agents, thickeners, moisturizers, emollients, pharmaceutical actives, vitamins or nutrients, anti-dandruff agents, perfumes, hair colorants, hair perming agents, hair growth or restorer agents, and similar other materials.

The personal care composition may also comprise one or more processing aids, selected from the group consisting of water, aggregate inhibiting materials such as divalent salts; particle suspending polymers such as xanthan gum, guar gum, and carboxy methyl cellulose. In another embodiment, said processing aids may be selected from the group consisting of amphoteric surfactants such as cocamidopropyl betaine (CAPB), zwitterionic surfactants, cationic swellable polymers, latex particles such as acrylic based ester Rheovis CDE, and mixtures thereof.

In one aspect, the personal care composition may comprise a carrier selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

In another embodiment, the personal care composition may comprise a material selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

In another embodiment, the personal care composition may comprise structuring agents selected from the group consisting of castor oil, polysaccharides, and combinations thereof.

TEST METHODS

It is understood that the test methods that are disclosed in the Test Methods Section of the application should be used to determine the respective values of the parameters of Applicants' invention as such invention is described and claimed herein.

A. Median Particle Size

The volume-average mean particle size of the emulsified stabilizing agent can be measured by a Horiba Laser Scattering Particle Size Distribution Analyzer, model LA-950 from Horiba Instruments, Ann Arbor, Mich. The measurement should be performed at a temperature of 5 C above the melting point of the stabilizing agent, to keep the emulsion droplets from crystallizing prior to the particle-size measurement.

B. Viscosity

The stabilizing premix has a viscosity from 1 to 1500 centipoises (1-1500 mPa*s), in another embodiment from 100 to 1000 centipoises (100-1000 mPa*s), and in another embodiment from 200 to 500 centipoises (200-500 mPa*s) at $2\ s^{-1}$ and 25° C., when measured one day after making Viscosity is measured using an AR2000 rheometer from TA instruments with a 40 mm diameter steel plate fixture and a gap size of 500 μm.

C. Crystal Morphology

The crystal morphology in the stabilizing premix can be characterized via light microscopy or by Scanning Electron Microscopy, as described in FR2906715A1.

EXAMPLES

Exemplary personal care compositions, in accordance with the principles of this disclosure, can be prepared as set forth in Table 1 (Stabilizing Premix) and Table 2 (Personal Care Compositions).

TABLE 1

Stabilizing Premix

| Example | 1 | 2 | 3 |
|---|---|---|---|
| Ethylene glycol distearate | 18% | 18% | 18% |
| sodium laureth-1 sulfate | 5% | 5% | 5% |
| cetyl alcohol | 0% | 1.25% | 2.50% |
| sodium benzoate | 0.25% | 0.25% | 0.25% |
| water | qs | qs | qs |

TABLE 2

Personal Care Composition

| Example | 1 | 2 | 3 |
|---|---|---|---|
| sodium laureth-1 sulfate | 12.5% | 12.5% | 12.5% |
| ethylene glycol distearate | 2% | 2% | 2% |
| zinc carbonate | 1.61% | 1.61% | 1.61% |
| zinc pyrithione | 1% | 1% | 1% |
| cocoamidopropyl betaine | 1% | 1% | 1% |
| fragrance | 0.80% | 0.80% | 0.80% |
| cetyl alcohol | 0% | 0.139% | 0.278% |
| sodium bnzoate | 0.25% | 0.25% | 0.25% |
| guar hydroxypropyltrimonium | 0.23% | 0.23% | 0.23% |
| sodium chloride | 0.50% | 0.44% | 0.42% |
| water | qs | qs | qs |

Example 1

138 kg of water, 42.6 kg of 26% active sodium laureth-1 sulfate (Stepan, Elwood, Ill.), and 0.55 kg of sodium benzoate are added to a 250 L jacketed stirred tank. The contents are heated and mixed for 30 minutes with a pitched-blade-turbine impeller at 50 revolutions per minute (rpm) to a temperature of 70 C, then 39.7 kg of ethylene glycol distearate (Evonik, Hopewell, Va.) at 75 C is added and mixed at 90 rpm for ten minutes to achieve a final batch temperature of 73 C. The composition is pumped at a flow rate of 25 kg/min through a DR3-6 (IKA Works, Wilmington, N.C.) rotor-stator mill followed by an Alfa Laval (Richmond, Va.) M10b plate-and-frame heat exchanger in a single-pass cooling to 26 C to create a stabilizing premix (See Table 1). The DR3-6 mill is equipped with three fine sets of rotor-stators and operated at a tip speed of 22 m/sec. The outlet temperature of the composition is controlled by manipulating the flow rate of 6 C water into the utility side of the heat exchanger, using a counter-current cooling configuration.

77.8 g of the stabilizing premix described in the preceding paragraph is combined with 622 g of a personal care base composition to form 700 g of a personal care composition comprising 12.5% sodium laureth-1 sulfate, 2% ethylene glycol distearate, 1.61% zinc carbonate (Shepherd Chemical, Norwood, Ohio), 1% zinc pyrithione (Arch Chemicals, Rochester, N.Y.), 1% cocoamidopropyl betaine (Stepan, Elwood, Ill.), 0.8% fragrance, 0.25% sodium benzoate, and 0.23% guar hydroxypropyltrimonium (Rhodia, Vernon, Tex.). The resulting personal care composition is homogenized by mixing for four minutes at 800 rpm in a Speedmixer DAC 800.1 FVZ (FlackTek, Landrum, S.C.), with 3.5 g of sodium chloride added to increase the viscosity (measured at 26.7 C and a shear rate of 2/sec) to 10056 centipoise (cP).

85 g of the personal care composition is then poured into a 4 cm diameter glass jar, which is sealed and placed in a 40 C stability chamber. The sample jar is monitored daily until 3 mm of a clear phase separates at the top of the sample. For Example 1 this clear phase separation occurred 20 days after the sample was placed in the 40 C chamber.

Example 2

140 kg of water, 44.3 kg of 26% active SLE1S, 2.88 kg of cetyl alcohol (BASF, Beaumont, Tex.) and 0.575 kg of sodium benzoate is added to a 250 L jacketed stirred tank. The contents are heated and mixed for 30 minutes with a pitched-blade-turbine impeller at 50 rpm to a temperature of 70 C, then 41.4 kg of 75 C EGDS at 75 C is added and mixed at 90 rpm for ten minutes to achieve a final batch temperature of 72 C. The composition is then pumped at a flow rate of 18 kg/min through a DR3-6 rotor-stator mill followed by an Alfa Laval M10b plate-and-frame heat exchanger in a single-pass cooling to 28 C to create a stabilizing premix. The DR3-6 mill is equipped with three fine sets of rotor-stators and operated at a tip speed of 20 m/sec. The outlet temperature of the composition is controlled by manipulating the flow rate of 7 C water into the utility side of the heat exchanger, using a counter-current cooling configuration.

77.8 g of the stabilizing premix described in the preceding paragraph is combined with 622 g of a homogeneous personal care base composition to form 700 g of a personal care composition comprising 12.5% sodium laureth-1 sulfate, 2% EGDS, 1.61% zinc carbonate, 1% zinc pyrithione, 1% cocoamidopropyl betaine, 0.8% fragrance, 0.25% sodium benzoate, 0.23% guar hydroxypropyltrimonium, and 0.139% cetyl alcohol. The resulting personal care composition is homogenized by mixing for four minutes at 800 rpm in a Speeedmixer DAC 800.1 FVZ, with 3.1 g of sodium chloride added to increase the viscosity (measured at 26.7 C and a shear rate of 2/sec) to 9350 cP.

85 g of the personal care composition is then poured into a 4 cm diameter glass jar, which is then sealed and placed in a 40 C stability chamber. The sample jar is monitored weekly until 3 mm of a clear phase separates at the top of the sample. For Example 2 this clear phase separation occurred 8 weeks after the sample was placed in the 40 C chamber.

Example 3

137.5 kg of water, 44.3 kg of 26% active SLE1S, 5.74 kg of cetyl alcohol and 0.575 kg of sodium benzoate are added to a 250 L jacketed stirred tank. The contents are heated and mixed for 30 minutes with a pitched-blade-turbine impeller at 50 rpm to a temperature of 70 C, then 41.4 kg of EGDS at 75 C are added and mixed at 90 rpm for ten minutes to achieve a final batch temperature of 73 C. The composition is then pumped at a flow rate of 25 kg/min through a DR3-6 rotor-stator mill followed by an Alfa Laval M10b plate-and-frame heat exchanger in a single-pass cooling to 33 C to create a stabilizing premix. The DR3-6 mill is equipped with three fine sets of rotor-stators and operated at a tip speed of 22 m/sec. The outlet temperature of the composition is controlled by manipulating the flow rate of 7 C water into the utility side of the heat exchanger, using a counter-current cooling configuration.

77.8 g of the stabilizing premix described in the preceding paragraph is combined with 622 g of a homogeneous personal care base composition to form 700 g of a personal care composition comprising 12.5% sodium laureth-1 sulfate, 2% EGDS, 1.61% zinc carbonate, 1% zinc pyrithione, 1% cocoamidopropyl betaine, 0.8% fragrance, 0.278% cetyl alcohol, 0.25% sodium benzoate, and 0.23% guar hydroxypropyltrimonium. The resulting personal care composition is homogenized by mixing for four minutes at 800 rpm in a Speeedmixer DAC 800.1 FVZ, with 3.0 g of sodium chloride added to increase the viscosity (measured at 26.7 C and a shear rate of 2/sec) to 9930 cP.

85 g of the personal care composition is then poured into a 4 cm diameter glass jar, which is then sealed and placed in a 40 C stability chamber. The sample jar is monitored weekly until 3 mm of a clear phase separates at the top of the sample. For Example 3 this clear phase separation occurred 16 weeks after the sample was placed in the 40 C chamber.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a stable, detersive surfactant-containing antimicrobial personal care composition, said method comprising:
    (a) emulsifying from about 4% to about 30% of a stabilizing agent in the presence of about 2% to about 30% of an anionic surfactant at a temperature of about 70° C. to about 75° C. to form an emulsion, wherein:
        (i) the stabilizing agent is ethylene glycol distearate (EGDS),
        (ii) the anionic surfactant is selected from the group consisting of an alkyl sulfate, an alkyl ether sulfate, or a combination thereof, and
        (iii) the formed emulsion contains droplets having a particle size of about 0.1 to about 10 µm;
    (b) cooling the emulsion of step (a) at a rate of about 10 to about 1000° C./minute to a temperature of about 25° C. to about 35° C. to form a stabilizing premix, wherein the stabilizing premix comprises crystals formed from the emulsion droplets, said crystals having a mean length of about 0.1 to about 3 µm and an aspect ratio of about 2 to about 1000; and
    (c) adding the stabilizing premix of step (b) to a detersive surfactant-containing antimicrobial personal care composition.

2. The method of claim 1, wherein the stabilizing premix comprises from about 4% to about 40% of the total detersive surfactant containing personal care composition.

3. The method of claim 1, wherein the alkyl ether sulfate has a molar ethoxylation ratio of from about 0.5 to about 5.

4. The method of claim 1, wherein the emulsion of the crystallizing agent employs an agitated tank, a static mixer, an orifice plate, a rotor/stator mill, high energy homogenizer, or combinations thereof.

5. The method of claim 4, wherein the high energy homogenizer is a sonolator.

6. The method of claim 1, wherein the emulsion is created using a power density of from about 1 to about 1000 W/kg.

7. The method of claim 1, wherein the stabilizing premix is added to the detersive surfactant containing personal care composition less than 24 hours after crystallization.

8. The method of claim 1, wherein the viscosity of the stabilizing premix is from about 50 to about 20,000 cP.

9. The method of claim 1, wherein the cooling of the emulsion employs a heat exchanger in a single pass or recirculation process.

10. The method of claim 9, wherein the heat exchanger is a scraped wall, plate and frame, or shell and tube heat exchanger.

11. The method of claim 1, wherein the personal care composition contains an additional structuring agent selected from the group consisting of hydrogenated castor oil, polysaccharides, and combinations thereof.

12. The method of claim 1, wherein the personal care composition contains detersive surfactants selected from the group consisting of anionic surfactants, zwitterionic surfactants, amphoteric surfactants, or combinations thereof.

13. The method of claim 1, wherein both the stabilizing premix and the personal care composition comprise at least 2% of the same anionic surfactant.

14. The method of claim 1, wherein the anti-microbial personal care composition is an anti-dandruff active and wherein the anti-dandruff active is ZPT.

15. The method of claim 1, wherein the personal care composition containing crystals separates less than 4 mm in about 30 days when 85 g of the anti-microbial personal care composition is placed in a 5 cm diameter jar at 40° C.

* * * * *